United States Patent
Akiyama et al.

(10) Patent No.: US 10,040,700 B2
(45) Date of Patent: Aug. 7, 2018

(54) ULTRAVIOLET TREATMENT APPARATUS AND LIGHT-SHIELDING COMPONENT THEREFOR

(71) Applicant: PHOTOSCIENCE JAPAN CORPORATION, Hachioji-shi, Tokyo (JP)

(72) Inventors: Noboru Akiyama, Higashimurayama (JP); Yuji Yamakoshi, Taito-ku (JP)

(73) Assignee: PHOTOSCIENCE JAPAN CORPORATION, Tokyo (JP)

( * ) Notice: Subject to any disclaimer, the term of this patent is extended or adjusted under 35 U.S.C. 154(b) by 0 days.

(21) Appl. No.: 15/556,502

(22) PCT Filed: Mar. 9, 2016

(86) PCT No.: PCT/JP2016/057447
§ 371 (c)(1),
(2) Date: Sep. 7, 2017

(87) PCT Pub. No.: WO2016/143829
PCT Pub. Date: Sep. 15, 2016

(65) Prior Publication Data
US 2018/0072590 A1    Mar. 15, 2018

(30) Foreign Application Priority Data
Mar. 11, 2015 (JP) ................................ 2015-048628

(51) Int. Cl.
*A61L 2/10* (2006.01)
*C02F 1/32* (2006.01)
(Continued)

(52) U.S. Cl.
CPC ................ *C02F 1/325* (2013.01); *A61L 2/10* (2013.01); *A61L 2/26* (2013.01); *A61L 2202/11* (2013.01);
(Continued)

(58) Field of Classification Search
CPC .. C02F 1/325; C02F 2103/04; C02F 2303/04; A61L 2/26; A61L 2/10; A61L 2202/11; A61L 2202/121
(Continued)

(56) References Cited

U.S. PATENT DOCUMENTS 5,372,781 A * 12/1994 Hallett ...................... A61L 2/10
422/186

FOREIGN PATENT DOCUMENTS

JP    HEI01092296 U    6/1989
JP    HEI03098940 U    10/1991
(Continued)

OTHER PUBLICATIONS

International Search Report issued in Intl. Appln. No. PCT/JP2016/057447 dated Jun. 14, 2016. English translation provided.
(Continued)

*Primary Examiner* — Michael Maskell
(74) *Attorney, Agent, or Firm* — Rossi, Kimms & McDowell LLP

(57) ABSTRACT

A light-shielding strip, for preventing a sealing member from deterioration due to ultraviolet rays, is made of a ultraviolet-shielding material having a resilient plate shape, and comprises: a main light-shielding portion having a length according to at least a circumferential length of an inner periphery of a lamp-protective tube; and first and second overlap portions extending from respective ones of both ends of the main light-shielding portion in a longitudinal direction with each forming a non-parallel convergence shape. The light-shielding strip, rolled in the longitudinal direction, is disposed in the lamp-protective tube to closely fit to the inner periphery of the lamp-protective tube and positioned to oppose to the sealing member. Repulsive force against bending force around an end portion of the (Continued)

light-shielding strip can be dispersed due to the non-parallel convergence shape of the overlap portions, so that a possible-raised portion around the end portion can be suppressed.

16 Claims, 4 Drawing Sheets

(51) Int. Cl.
*A61L 2/26* (2006.01)
*C02F 103/04* (2006.01)

(52) U.S. Cl.
CPC ..... *A61L 2202/121* (2013.01); *C02F 2103/04* (2013.01); *C02F 2303/04* (2013.01)

(58) Field of Classification Search
USPC ............................ 250/453.11–455.11, 504 R
See application file for complete search history.

(56) References Cited

FOREIGN PATENT DOCUMENTS

| JP | HEI06029160 U | 4/1994 |
|----|---------------|--------|
| JP | H1048760 A | 2/1998 |
| JP | H11274612 A | 10/1999 |
| JP | 2002270010 A | 9/2002 |
| JP | 2002282851 A | 10/2002 |
| JP | 2003123630 A | 4/2003 |
| JP | 2005063986 A | 3/2005 |
| JP | 2014159029 A | 9/2014 |

OTHER PUBLICATIONS

Written Opinion issued in Intl. Appln. No. PCT/JP2016/057447 dated Jun. 14, 2016.
International Preliminary Report on Patentability issued in Intl. Appln. No. PCT/JP2016/057447 dated Dec. 13, 2016. English translation provided.

* cited by examiner

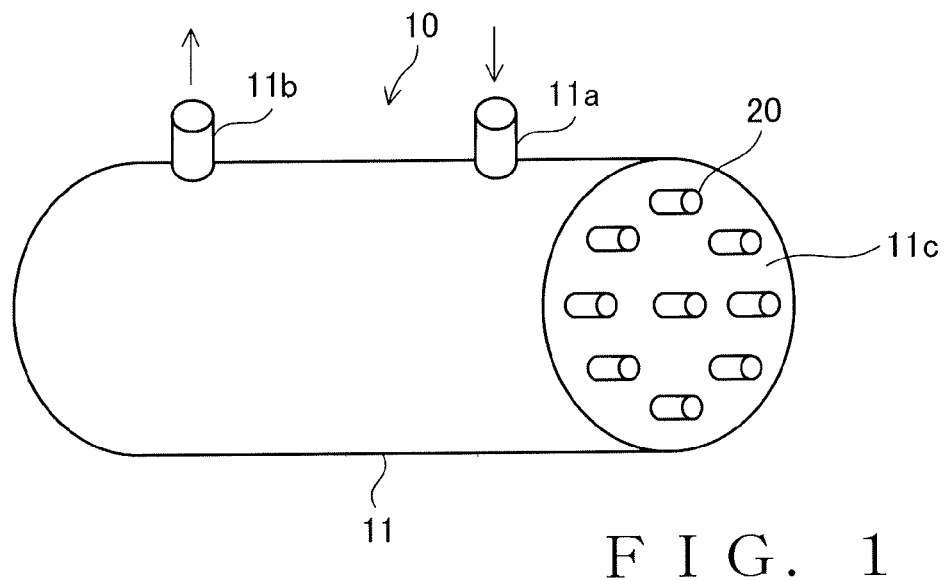
F I G. 1
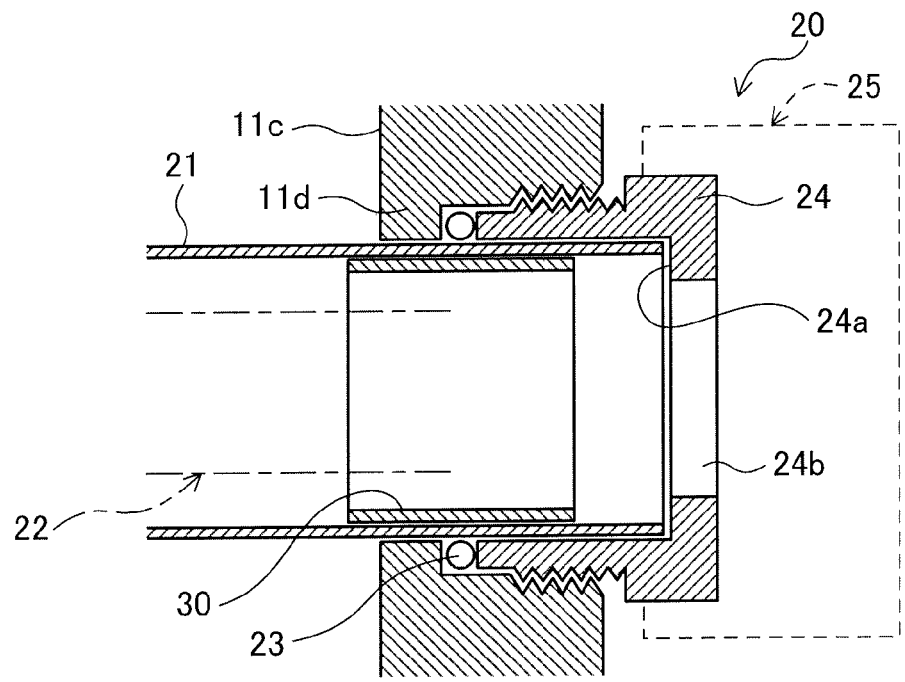
F I G. 2

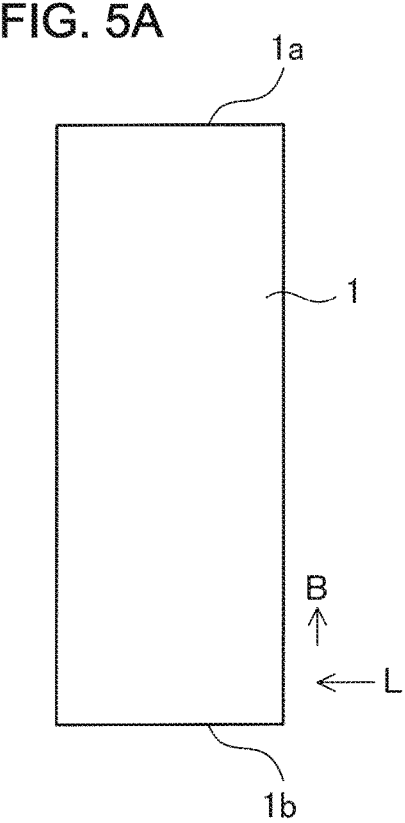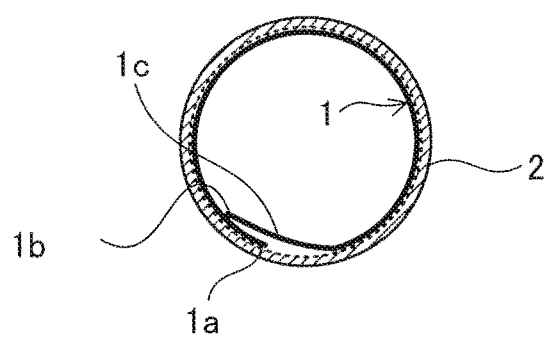

US 10,040,700 B2

ULTRAVIOLET TREATMENT APPARATUS AND LIGHT-SHIELDING COMPONENT THEREFOR

TECHNICAL FIELD

The present invention relates to an ultraviolet treatment apparatus, particularly relates to an improvement of light-shielding means for preventing a sealing member, such as an O-ring for sealing a container, from deterioration due to ultraviolet rays, and relates to a light-shielding component therefor.

BACKGROUND ART

Ultrapure water is used in a manufacturing process of products in semiconductor factories, FPD (flat panel display) factories or the like. Among items of water quality for the ultrapure water, there are the number of viable bacteria and the density of TOC (total organic carbon). An ultraviolet sterilization apparatus is employed in the ultrapure water production process as a facility for inactivating microbes, and a low pressure UV oxidation apparatus is employed in the ultrapure water production process as one of facilities for reducing the concentration of TOC. These apparatus provide with one or more low-pressure mercury lamps emitting ultraviolet rays of 254 nm or 185 nm wavelength which are contained in a cylindrical reactor vessel. Each of the lamps is inserted in a lamp-protective tube made of quartz so that the lamp never directly contacts water to be treated or processed in the vessel. The to-be-treated water flows between the outside of the protective tube and the inside of the vessel in a pressurized condition while exposed to ultraviolet rays. Microbes in the to-be-treated water are exposed to the ultraviolet rays of 254 nm wavelength and inactivated thereby. In general, such an exposure is also referred to as sterilization. Further, an OH radical is generated from the to-be-treated water exposed to the ultraviolet rays of 185 nm wavelength, and the TOC is decomposed by oxidation of the generated OH radical to the TOC. Simultaneously, organic substances in the water are directly decomposed by the ultraviolet rays of 254 nm and 185 nm wavelength emitted form the low-pressure mercury lamps. Reactions similar to the aforementioned can be occurred by means of a middle-pressure mercury lamp, a high-pressure mercury lamp, an excimer lamp or the like, not limited to the low-pressure mercury lamp. Quartz, sapphire, fluororesin, etc. are used for a material of the lamp-protective tube.

At least one end of the lamp-protective tube is supported by a wall of the vessel and exposed to the outside so that a lamp can be inserted in and pulled from the lamp-protective tube through the one end exposed to the outside. Further, an elastic sealing member is provided on a portion where the lamp-protective tube is supported in the vessel so that the sealing member adheres to an outer periphery of the lamp-protective tube to seal the inside of the vessel. Typically, the sealing member is an O-ring made of rubber. However, because the ultraviolet rays are irradiated onto not only the to-be-treated water but also the sealing member (O-ring) considerably, accumulation of the irradiation brings the O-ring deterioration due to the ultraviolet rays that causes a possibility of a defect, i.e. water leakage. Particularly, in a case where an output of the low-pressure mercury lamp is increased and quartz having high transmissivity with respect to the 254-nm or 185-nm wavelength is used for the lamp and the lamp-protective tube, the O-ring intends to deteriorate because of the ultraviolet rays within a relatively short period.

It should be noted that there is a known prior art, as indicated in patent literatures listed below, which is constructed to prevent peripheral components from deterioration by light-shielding a part of a light source or a device integrally incorporated in the light source. Patent Literatures 1 and 2 disclose to provide with a ring-shaped UV-shielding member in order to prevent a plastic insulation plug from deterioration due to ultraviolet rays which have leaked through a side of an end portion of a power connection of an arc tube emitting the ultraviolet rays. Patent Literature 3 discloses that, in an ultraviolet treatment apparatus which is configured to emit ultraviolet rays into space from a plurality of UV lamps disposed in parallel with each other and irradiate them to an object to be treated, a UV-shielding membrane is provided on each adjacent side of each of the UV lamps in order to reduce an effect, of the ultraviolet rays emitted from each lamp, to each of adjacent lamps.

Patent Literature 4 discloses that, in a window for an excimer laser, in order to prevent an O-ring for sealing laser medium gas from deterioration due to ultraviolet rays, membranes not transmitting the ultraviolet rays are vapor-deposited on closely-adjacent surfaces of the window and the O-ring, and thereafter, each of the deposited membranes is filmed with an oxidation protective membrane. Patent Literature 5 discloses that, in a solid laser oscillator, in order to prevent an O-ring for liquid-tightly sealing an end of a filter cylinder from deterioration due to excitation rays, a light-shielding ring is provided so as to shield a light leak from an end of an excitation lamp. Patent Literature 6 discloses that, in order to prevent an O-ring for keeping airtightness of a plasma treatment chamber from deterioration, plasma shielding means, which consists of a steel plate in a shape of a thin metallic belt having been wound in a spiral or a conductor wire having been wound in a shape of a solenoid coil or having been netted in a cylindrical shape, is put into a circular groove formed on a side nearer the treatment chamber than another circular groove putting the O-ring thereinto.

However, none of devices disclosed in the aforementioned Patent Literatures is suitable for such a construction as mentioned above that the O-ring is disposed so as to adhere to the outer periphery of the lamp-protective tube. In such a construction, it is necessary for a UV-shielding member to be disposed within the lamp-protective tube. According to the aforementioned Patent Literatures, it is conceivable that the UV-shielding member in a shape of a cylindrical ring is disposed within the lamp-protective tube. In a case where a cylindrical-shaped light-shielding ring is to be employed, it would be ordinary for a skilled engineer to adopt such a construction that employs a light-shielding ring having an outer diameter slightly smaller than an inner diameter of the lamp-protective tube so as to facilitate work for inserting the light-shielding ring into the lamp-protective tube. If so, however, because the light-shielding ring becomes slightly loose in the lamp-protective tube, there would be a problem that, when a UV lamp in the lamp-protective tube should be replaced, the light-shielding ring tends to move because of contact with a base of the UV lamp moving for replacement, so that troublesome correction of a location of the disposed light-shielding ring is required, and that the contact between the light-shielding ring and the base of the UV lamp disturbs a motion of inserting or pulling the lamp. Thus, it is not preferable to dispose the cylindricalring-shaped UV-shielding member having a fixed diameter within the lamp-protective tube.

PRIOR ART LITERATURE

Patent Literature

Patent Literature 1: Japanese Patent Application Laid-open No. 2002-270010
Patent Literature 2: Japanese Patent Application Laid-open No. 2003-123630
Patent Literature 3: Japanese Patent Application Laid-open No. 2014-159029
Patent Literature 4: Japanese U.M. Application Laid-open No. 1994-029160
Patent Literature 5: Japanese Patent Application Laid-open No. 1999-274612
Patent Literature 6: Japanese Patent Application Laid-open No. 2005-063986

By contrast, it is conceivable that a ring-like UV-shielding member is composed by a resilient metallic plate material rolled and disposed in the lamp-protective tube. In this way, it is expected that the UV-shielding member becomes hard to move loosely in the lamp-protective tube because the rolled ring-like plate material tends to adhere an inner periphery of the lamp-protective tube by reason of resiliency of the plate material itself. However, according to an analysis by the inventor, in a case where a rectangular UV-shielding plate material 1 as shown in FIG. 5(a) is employed, it was proved that, when the UV-shielding plate material 1 was disposed in a lamp-protective tube 2 so as to adhere an inner periphery of the lamp-protective tube 2 with the plate material 1 rolled in a longitudinal direction, such a phenomenon occurred that the vicinity of one end portion 1b of plate material 1 located in the inside of a roll of the plate material 1 was slightly raised while another end portion 1a located in the outside of the roll adhered the inner periphery of the lamp-protective tube 2, as shown in a sectional view of FIG. 5(b). Therefore, similarly to the case of the aforementioned cylindrical-ring-shaped UV-shielding member, there would be a problem that, when a UV lamp in the lamp-protective tube should be replaced, the light-shielding plate material tends to move because a raised portion 1c near the end portion 1b contacts a base of the UV lamp moving for replacement, so that troublesome correction of a location of the disposed light-shielding plate material is required, and that the contact between the light-shielding ring and the base of the UV lamp disturbs a motion of inserting or pulling the lamp.

SUMMARY OF THE INVENTION

In view of the foregoing, it is an object of the present invention to provide an improved light-shielding member (i.e. light-shielding component) for preventing a sealing member from deterioration due to ultraviolet rays in an ultraviolet treatment apparatus which includes the sealing member disposed so as to closely contact an outer periphery of a lamp-protective tube, wherein the light-shielding member is constructed in such a manner as to never interfere with extraction or insertion of an ultraviolet lamp accommodated in the lamp-protective tube.

In order to accomplish the above-mentioned object, the present invention provides an ultraviolet treatment apparatus comprising: an ultraviolet lamp; a lamp-protective tube that inserts the ultraviolet lamp therein; a container that accommodates and supports the lamp-protective tube with at least one end of the lamp-protective tube exposed to an exterior, an object to be treated being introduced into the container; and a sealing member that seals the container by closely contact an outer periphery of the lamp-protective tube at a portion of the container where the lamp-protective tube is supported, characterized in that the ultraviolet treatment apparatus further comprises: a light-shielding strip made of a ultraviolet-shielding material and having resiliency, the light-shielding strip comprising: a main light-shielding portion having a length according to at least a circumferential length of an inner periphery of the lamp-protective tube; and first and second overlap portions extending from respective ones of both ends of the main light-shielding portion in a longitudinal direction with each forming a non-parallel convergence shape, wherein the light-shielding strip, rolled in the longitudinal direction, is disposed in the lamp-protective tube so as to closely fit to the inner periphery of the lamp-protective tube and positioned so as to oppose to the sealing member.

Further, in order to accomplish the above-mentioned object, the present invention provides an improved light-shielding component to be employed in an ultraviolet treatment apparatus which comprises: an ultraviolet lamp; a lamp-protective tube that inserts the ultraviolet lamp therein; a container that accommodates and supports the lamp-protective tube with at least one end of the lamp-protective tube exposed to an exterior, an object to be treated being introduced into the container; and a sealing member that seals the container by closely contacting an outer periphery of the lamp-protective tube at a portion of the container where the lamp-protective tube is supported, the light-shielding component comprising: a light-shielding strip made of a ultraviolet-shielding material and having resiliency, the light-shielding strip comprising: a main light-shielding portion having a length according to at least a circumferential length of an inner periphery of the lamp-protective tube; and first and second overlap portions extending from respective ones of both ends of the main light-shielding portion in a longitudinal direction with each forming a non-parallel convergence shape, wherein, when the light-shielding component is employed in the ultraviolet treatment apparatus, the light-shielding strip, rolled in the longitudinal direction, is disposed in the lamp-protective tube so as to closely fit to the inner periphery of the lamp-protective tube and positioned so as to oppose to the sealing member.

According to the present invention, the light-shielding component comprises the resilient light-shielding strip composed of the main light-shielding portion and the first and second overlap portions, and in a state where the light-shielding strip is rolled and disposed in the lamp-protective tube, the light-shielding strip is to be rolled with the first and second overlap portions overlapping the main light-shielding portion. In this way, because the resilient light-shielding strip is rolled and disposed in the lamp-protective tube, the thus-rolled light-shielding strip forms a ring or cylindrical shape and tends to adhere to the inner periphery of the lamp-protective tube due to the resiliency of the light-shielding strip itself, so that there is no fear for the light-shielding strip moving loosely in the lamp-protective tube. Further, because the light-shielding strip is composed of the main light-shielding portion and the first and second overlap portions extending from respective ones of the both ends of the main light-shielding portion and the main light-shielding portion has the length according to at least the circumferential length of the inner periphery of the lamp-protective tube, once the light-shielding strip has been rolled to form the ring or cylindrical shape, it is possible to suitably cover a portion of the inner periphery of the lamp-protective tube, opposing to the sealing member, with the main light-shielding portion, so that light-shielding performance to the sealing member is secured. Moreover, because the first and second overlap portions extend from the respective ones of both ends of the main light-shielding portion in the longitudinal direction and each of the first and second overlap portions forms the non-parallel convergence shape, it is achievable to disperse repulsive force against bending force around both end portions of the light-shielding strip due to the non-parallel convergence shape, so that a possible-raised portion such as the raised portion 1c as shown in FIG. 5(b) can be suppressed. Namely, it seems that, in the UV-shielding plate material 1 of a simple rectangle shape as shown in FIG. 5(a), because the end portion 1b forms a straight line in a direction of arrow L, repulsive force against bending force effected in a right-angled direction B at a position along the arrow L is produced over the whole of the straight line of the end portion 1b, so that the repulsive force against the bending force becomes to maximum to thereby produce the raised portion 1c around the vicinity of the end portion 1b. By contrast, according to the present invention, because each of the first and second overlap portions forming the both end portions of the light-shielding strip forms the non-parallel convergence shape, it is achievable to disperse the repulsive force against the bending force around the both end portions of the light-shielding strip, so that a partial raise of the light-shielding strip around the end portion thereof can be suppressed. In this way, according to the present invention, it is achieved to provide such a light-shielding member that is constructed so as to never interfere with extraction or insertion of the ultraviolet lamp accommodated in the lamp-protective tube, and also there is no such a problem that, when the ultraviolet lamp in the lamp-protective tube should be replaced, the disposed position of the light-shielding member is displaced due to contact of the light-shielding member to a base of the lamp or the like.

BRIEF DESCRIPTION OF DRAWINGS

FIG. 1 is a perspective view schematically illustrating an appearance of an ultraviolet treatment apparatus in accordance with an embodiment of the present invention;

FIG. 2 is an enlarged schematic longitudinal section view of one end portion of an ultraviolet lamp unit shown in FIG. 1;

FIGS. 5A and 5B are a set of diagrams illustrating a problem of a conceivable rectangular light-shielding plate material.

DESCRIPTION OF EMBODIMENTS

Figure 3A:
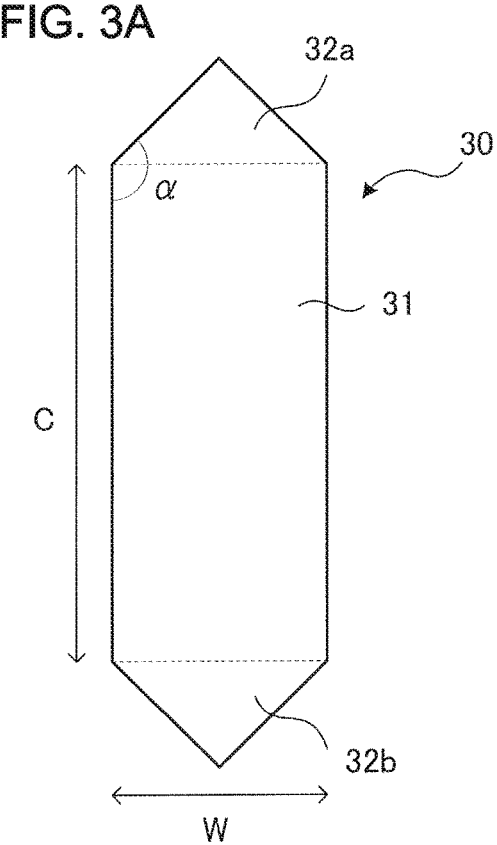
FIG. 3A is a plan view illustrating an example of a light-shielding strip developed in a flat-plate shape before rolled up.

FIG. 1 is a perspective view schematically illustrating an appearance of an ultraviolet treatment apparatus 10 according to an embodiment of the present invention, which performs ultraviolet treatment of an object, e.g., liquid, and particularly performs ultrapure water treatment like the aforementioned ultrapure water production process. A container 11 has an inlet 11a for taking liquid as an object to be treated therein and an outlet 11b for discharging the liquid having been treated therefrom. A plurality of ultraviolet lamp units 20 are provided in the container 11. Since each of the plurality of ultraviolet lamp units 20 may be the same construction as each other, a detailed description about only one ultraviolet lamp unit 20 will be made hereinafter.

FIG. 2 is an enlarged schematic longitudinal section view of one end portion of the one ultraviolet lamp unit 20. The ultraviolet lamp unit 20 includes a transparent lamp-protective tube 21 having permeability to ultraviolet light and an ultraviolet lamp 22 to be inserted in the lamp-protective tube 21. A through hole is pierced at a predetermined position on an end wall 11c of the reactor container 11 so as to allow the lamp-protective tube 21 to be inserted in the container 11, so that the lamp-protective tube 21 is inserted in the container 11 via the through hole and supported by the end wall 11c of the container 11 with one end of the lamp-protective tube 21 exposed to an exterior. An O-ring 23 made of rubber (i.e., a sealing member for sealing the container 11) is arranged at a portion of the end wall 11c of the container 11, where the lamp-protective tube 21 is supported, so that the O-ring 23 adheres to an outer periphery of the lamp-protective tube 21. A female screw is provided on a predetermined portion, adjacent to the exterior, of an inner periphery of the through hole, so that the female screw is coupled with a male screw provided on a cap 24 for fixing the end of the lamp-protective tube 21 to the end wall 11c of the container 11. When the cap 24 is screwed in a tightening direction at the end of the container 11 in a state where the O-ring 23 is put on the outer periphery of the lamp-protective tube 21 in a suitable position near the end of the lamp-protective tube 21, the male screw provided on the cap 24 is coupled with the female screw provided on the through hole of the end wall 11c of the container 11, so that the cap 24 is advanced left in FIG. 2. The ultraviolet lamp 22 is a type of capable of emitting ultraviolet rays of wavelengths less than 300 nm, e.g., 185 nm-wavelength and 254 nm-wavelength.

An inner portion of the through hole of the end wall 11c of the container 11 forms a small diameter portion 11d having a size capable of adhering to the outer periphery of the lamp-protective tube 21, and functions as a section for supporting the outer periphery of the lamp-protective tube 21 as well as a stopper for stopping the O-ring 23 at the position of the small diameter portion 11d. When the cap 24 is screwed in the tightening direction, a distal end of the cap 24 advancing left in FIG. 2 pushes the O-ring 23 away, and then the pushed O-ring 23 is tightly pressed and stopped at the position of the small diameter portion 11d, so that the inside of the container 11 is sealed in a liquid-tight manner. In such a sealed condition, one end of the lamp-protective tube 21 may contact an inward flange 24a of the cap 24 or may be spaced out of the inward flange 24a with a gap (e.g., of several millimeters). The one end of the lamp-protective tube 21 forms an opening end, and an inside of the inward flange 24a forms an opening 24b too. The inside of the lamp-protective tube 21 communicates with the exterior of the container 11 through the opening 24b so that the lamp 22 can be inserted in and extracted (or pulled) from the lamp-protective tube 21. Further, although the outside of the cap 24 may be covered with a cover 25 such that a connecter, etc. for the lamp 22 can be contained therein, a detailed description thereof is omitted because of a well-known construction.

A light-shielding strip 30 that is an example of a light-shielding component according to the present invention is composed of a resilient plate (strip) made of a ultraviolet-shielding material which is rolled and disposed in the lamp-protective tube 21, and the light-shielding strip 30 is positioned so as to oppose to the sealing member, so that ultraviolet rays directed to the O-ring 23 from the light-source lamp 22 inserted in the protective tube 21 are shielded. FIG. 3(a) is a plan view illustrating an example of the light-shielding strip 30 developed in a flat-plate shape before rolled up. The light-shielding strip 30 comprises two functional portions, one of which is a main light-shielding portion 31 having a length corresponding to at least a circumferential length C of an inner periphery of the lamp-protective tube 21; and another one is a set of first and second overlap portions 32a, 32b that extend from respective ones of both ends of the main light-shielding portion 31 in a longitudinal direction with each forming a non-parallel convergence shape. In an example as shown in FIG. 3(a), the main light-shielding portion 31 forms a rectangular shape having two sides approximately parallel with each other, and each of the first and second overlap portions 32a, 32b extending from the both ends of the main light-shielding portion 31 forms one non-parallel convergence shape (namely, a triangle shape) whose maximum traverse width is equal to or smaller than a width between the two sides of the main light-shielding portion 31. Needless to say, the main light-shielding portion 31 and the first and second overlap portions 32a, 32b form a unit made of a common material. In an example as shown in FIG. 3(a), each of the first and second overlap portions 32a, 32b forms an approximate isosceles triangle whose base is contiguous to the main light-shielding portion 31. In an example, the light-shielding strip 30 is made of stainless steel, and a thickness of the light-shielding strip 30 is about 0.1 mm.

Note that a width W of the main light-shielding portion 31 should have a length enough to shield ultraviolet rays directed to the O-ring 23 from the lamp-protective tube 21, and around 5 cm or the like would be sufficient, for example. The width W of the main light-shielding portion 31 corresponds to a length of the light-shielding strip 30 with regard to an axial direction of the tube (i.e., a longitudinal direction of a linear lamp 22) in the state where the light-shielding strip 30 is rolled and disposed in the lamp-protective tube 21. Namely, the light-shielding strip 30 rolled in a ring (or cylindrical) shape shields around the O-ring 23 from the ultraviolet rays within a range of the width W. Further, it should be noted that a minimum value allowable as the length of the main light-shielding portion 31 (i.e., the length in an inner circumferential direction in the lamp-protective tube 21) is not necessarily just the same as the circumferential length C of the inner periphery of the lamp-protective tube 21, and it may be shorter than the circumferential length C depending on the shape of the overlap portions 32a, 32b. Namely, there is a case where, even if the main light-shielding portion 31 does not completely cover the whole of the circumferential length C of the inner periphery of the lamp-protective tube 21, an insufficient portion can be covered with respective portions around bases of the respective overlap portions 32a, 32b adjacent to the both ends of the main light-shielding portion 31. For example, if an angle α (see FIG. 3(a)) formed between a long side of the main light-shielding portion 31 and one side of the overlap portion 32a is relatively large and the width W of the main light-shielding portion 31 is relatively long, the portions around the bases of the respective overlap portions 32a, 32b can sufficiently shield the O-ring 23 from the ultraviolet rays directed thereto. Of course, the length of the main light-shielding portion 31 (namely, the length in the inner circumferential direction in the lamp-protective tube 21) may be longer than the circumferential length C of the inner periphery of the lamp-protective tube 21, but it is not required to be unnecessarily long. In summary, the length of the main light-shielding portion 31 (namely, the length in the inner circumferential direction in the lamp-protective tube 21) may be a length according to at least the circumferential length C of the inner periphery of the lamp-protective tube 21 (including a length suitably shorter than the length C).

Figure 3B:
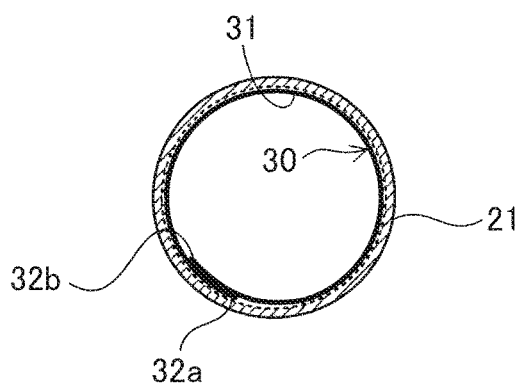
FIG. 3B is a traverse section view showing a state where the light-shielding strip is rolled in the longitudinal direction and disposed in a lamp-protective tube so as to closely fit to an inner periphery of the lamp-protective tube.

FIG. 3(b) is a traverse section view showing a state where the light-shielding strip 30 is rolled in the longitudinal direction and disposed in the lamp-protective tube 21 so as to closely fit to the inner periphery of the lamp-protective tube 21. In order for visibility, in FIG. 3(b), the inner periphery of the lamp-protective tube 21 is depicted by a dotted line, and a cross section of the light-shielding strip 30 is depicted by a bold solid line. Since the main light-shielding portion 31 of the light-shielding strip 30 has the length according to at least the circumferential length C of the inner periphery of the lamp-protective tube 21, when the light-shielding strip 30 is rolled in the ring shape, the respective overlap portions 32a, 32b overlap the main light-shielding portion 31 so as to suitably cover the whole of an inner circumference portion of the lamp-protective tube 21 opposed to the O-ring 23 with the main light-shielding portion 31 mainly (and, additionally, the portions around the bases of the respective overlap portions 32a, 32b), so that light-shielding performance to the O-ring 23 is secured. Further, since the first and second overlap portions 32a, 32b extend from respective ones of the both ends of the main light-shielding portion 31 in the longitudinal direction and each forms the non-parallel convergence shape (the approximate isosceles triangle in FIG. 3), it is achievable to disperse a repulsive force against a bending force around an end portion of the light-shielding strip 30 due to the non-parallel convergence shape. Namely, although a relatively great repulsive force must be generated at the end portion of each of the first and second overlap portions 32a, 32b because the end portion is a start point of rolling the strip 30, the repulsive force against the bending force in the rolling of the strip 30 does not become so much because portions to be bended around the end portion (namely, the vertex of the isosceles triangle) are of a point or a section having narrow width. Although width of the portions to be bended in the overlap portions 32a, 32b increases in accordance with nearness to the bases of the overlap portions 32a, 32b, repulsive forces at the portions to be bended do not become so much because other portions have already been bended. In this way, because the repulsive force against the bending force around the end portion of the light-shielding strip 30 can be dispersed, the whole of the light-shielding strip 30 rolled in the ring shape closely fits to the inner periphery of the lamp-protective tube 21 so that such a possible-raised portion around the end portion such as the raised portion as shown in FIG. 5(b) is never produced or can be suppressed so as to be unnoticeable.

As mentioned above, because the possible-raised portion around the end portion is never produced in the state where the light-shielding strip 30 is disposed in the lamp-protective tube 21 so as to closely fit to the inner periphery of the lamp-protective tube 21 with the light-shielding strip 30 rolled in the longitudinal direction, there is no such a problem that a base of the ultraviolet lamp 22 contacts the light-shielding strip 30 when the ultraviolet lamp 22 should be inserted in and/or pulled out of the lamp-protective tube 21.

Figure 4A:
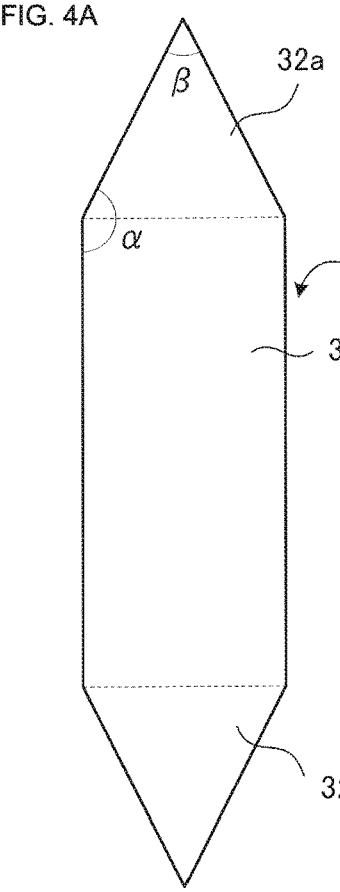
FIGS. 4A, 4B, 4C, 4D, and 4E are a set of plan views illustrating some modifications of the light-shielding strip.

The shape of the overlap portions 32a, 32b in the light-shielding strip 30 is not limited to the aforementioned approximate isosceles triangle, but the shape can be variously modified. Further, even in the case of the approximate isosceles triangle, various modifications of the shape can be employed such that the vertex makes an acute angle or obtuse angle, for example. FIG. 4 shows some modifications of the light-shielding strip 30. FIG. 4(a) shows such an example that the vertex β of the approximate isosceles triangle in each of the overlap portions 32a, 32b makes an acute angle. The more the acuteness of the vertex β increases, the more the angle α formed between the long side of the main light-shielding portion 31 and the one side of the overlap portion 32a increases and the more the degree of dispersion of the repulsive force against the bending force around the end portion of the light-shielding strip 30 increases, so that the possible-raised portion around the end portion is more suppressed. Needless to say, in order for the overlap portions 32a, 32b not to become too long, there is a limit to increase the acuteness of the vertex β. As an empirical example, the minimum angle value of the vertex β may be about 20 degrees or the like. In such a case, said angle α becomes about 170 degrees or the like. On the other hand, the vertex β of the approximate isosceles triangle in each of the overlap portions 32a, 32b may make an obtuse angle, and in such a case, the more the obtuseness of the vertex β increases, the less the angle α formed between the long side of the main light-shielding portion 31 and the one side of the overlap portion 32a decreases and the less the degree of dispersion of the repulsive force against the bending force around the end portion of the light-shielding strip 30 decreases, so that the degree of suppression of the possible-raised portion around the end portion is decreased. In order to realize necessary suppression of the possible-raised portion, there is a limit to increase the obtuseness of the vertex β. As an empirical example, the maximum angle value of the vertex β may be about 140 degrees or the like. In such a case, said angle a becomes about 110 degrees or the like. Therefore, it is conceivable that, as a guiding principle, it is better for the shape of the overlap portions 32a, 32b to be determined so that the angle α formed between the long side of the main light-shielding portion 31 and the one side of the overlap portion 32a or 32b falls into a range between about 110 to 170 degrees.

Figure 4B:
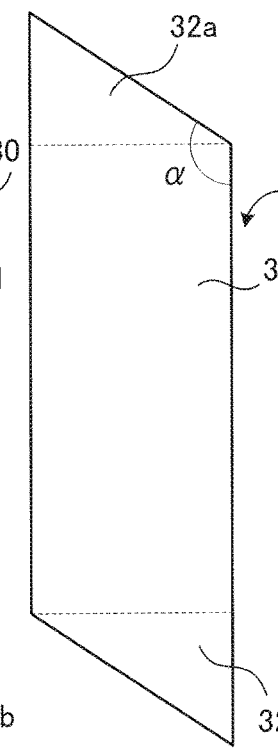
Figure 4C:
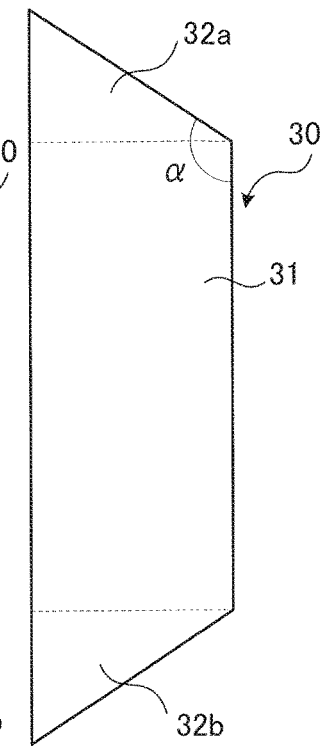
Figure 4D:
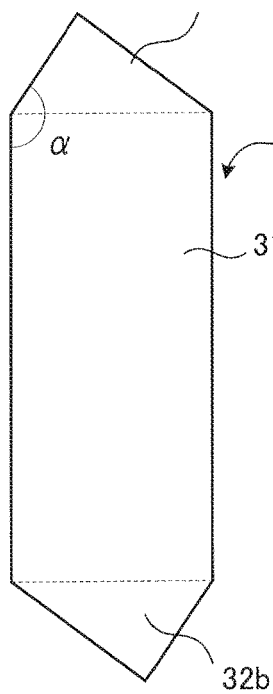

FIG. 4(b) shows such an example that each of the overlap portions 32a, 32b forms an approximate right-angled triangle and the whole of the light-shielding strip 30 forms an approximate parallelogram. FIG. 4(c) shows such an example that each of the overlap portions 32a, 32b forms an approximate right-angled triangle and the whole of the light-shielding strip 30 forms an approximate trapezoid. FIG. 4(d) shows such an example that each of the overlap portions 32a, 32b forms a scalene triangle. According to these shapes as well, the repulsive force against the bending force around the end portion of the light-shielding strip 30 can be dispersed, due to the non-parallel convergence shape of the overlap portions 32a, 32b, in a state where the light-shielding strip 30 is disposed in the lamp-protective tube 21 so as to closely fit to the inner periphery of the lamp-protective tube 21 with the light-shielding strip 30 rolled in the longitudinal direction, so that a possible-raised portion around the end portion is never produced or can be suppressed. It should be noted that, also in these cases, it is better for the shape of the overlap portions 32a, 32b to be determined so that the angle α formed between the long side of the main light-shielding portion 31 and the one side of the overlap portion 32a or 32b falls into the range between about 110 to 170 degrees.

Figure 4E:
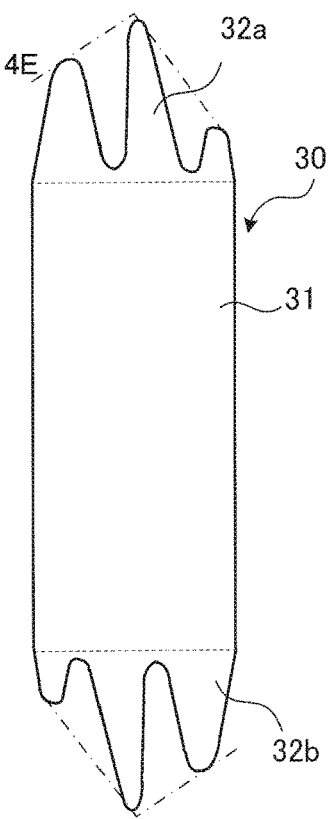

The number of the non-parallel convergence shape formed in each of the overlap portions 32a, 32b is not limited to one, but two or more shapes may be formed in each of the overlap portions 32a, 32b as shown in FIG. 4(e). In the light-shielding strip 30 having a plurality of the non-parallel convergence shapes in each of the overlap portions 32a, 32b as shown in FIG. 4(e), respective tip positions of the plurality of the non-parallel convergence shapes are deviated from each other so that a general outline of a scalene triangle shape or polygon shape is presented as indicated by a one dot chain line. In the case where the plurality of the non-parallel convergence shapes are formed in each of the overlap portions in this way, also, the repulsive force against the bending force around the end portion of the light-shielding strip 30 can be dispersed, due to the non-parallel convergence shape of the overlap portions 32a, 32b, in a state where the light-shielding strip 30 is disposed in the lamp-protective tube 21 so as to closely fit to the inner periphery of the lamp-protective tube 21 with the light-shielding strip 30 rolled in the longitudinal direction, so that a possible-raised portion around the end portion is never produced or can be suppressed.

Although the light-shielding strip 30 may be manufactured by metallic mold pressing, it is economical to be manufactured by etching processing or photoresist etching processing. Any one of materials among stainless steel, copper, nickel, iron, aluminum, aluminum alloy, gold, silver, molybdenum, titanium, amorphous, Kovar and silicon can be used for a material of the light-shielding strip 30 because these materials are suitable for the etching processing and have ultraviolet shielding ability. Further, in a case where any one of the materials except gold (namely, stainless steel, copper, nickel, iron, aluminum, aluminum alloy, silver, molybdenum, titanium, amorphous, Kovar and silicon) is used for a material of the light-shielding strip 30, a surface of the light-shielding strip 30 may be plated with gold. Further, a thickness of the light-shielding strip 30 may be in a range of 0.005 mm to 1 mm. In addition, every angle formed in the light-shielding strip 30 may be processed in order to round the angle, so that it becomes hard for the angle portion to be picked by something and a fear of a human worker's finger or the like harmed by an edged angle at the time of his/her working is eliminated.

Whereas two long sides of the main light-shielding portion 31 in the aforementioned embodiment linearly extend in parallel with each other, an embodiment of the present invention is not limited to such an arrangement, and the two long sides of the main light-shielding portion 31 may be gently curved rather than strict linear, for example.

It should be noted that either type of the ultraviolet lamp 22 which has a single base for electric connection provided on only one end of the lamp or double bases for electric connection provided on both ends of the lamp may be employed. In a case of the former type of the ultraviolet lamp, the lamp-protective tube 21 inserting the ultraviolet lamp 22 therein is supported by only one of end walls 11c provided on both ends of the container 11, and the lamp-protective tube 21 forms the opening at only one end of the tube corresponding to the one end wall 11c for support. In a case of the latter type of the ultraviolet lamp, the lamp-protective tube 21 inserting the ultraviolet lamp 22 therein is supported by both end walls 11c provided on both ends of the container 11 and forms the individual openings at both ends of the tube 21 corresponding to the both end walls 11c for support, and the aforementioned O-ring 23 and light-shielding strip 30 are dually provided too in corresponding relation with the both ends of the lamp-protective tube 21. Note that the present invention is not limited to be applied to a type of employing the O-ring 23 as the sealing member, but also can be applied to a type of employing any one of other suitable sealing members for fluid-tight or airtight such as a rubber packing.

Needless to say, the aforementioned light-shielding strip 30 may be distributed or sold not only along with the ultraviolet treatment apparatus 10 but also along with the ultraviolet lamp unit 20 or the lamp-protective tube 21, and moreover, the light-shielding strip 30 may be independently distributed or sold as an independent light-shielding component for use in the ultraviolet treatment apparatus 10 or the ultraviolet lamp unit 20. Further, the ultraviolet treatment apparatus according to the present invention is not limited to the aforementioned ultraviolet treatment apparatus 10 for liquid treatment, but also an ultraviolet sterilization apparatus for sterilizing and disinfecting an object to be treated arranged in an airy space is included in the scope of the ultraviolet treatment apparatus according to the present invention.

What is claimed is:

1. An ultraviolet treatment apparatus comprising:
   an ultraviolet lamp;
   a lamp-protective tube that inserts the ultraviolet lamp therein;
   a container that accommodates and supports the lamp-protective tube with at least one end of the lamp-protective tube exposed to an exterior, an object to be treated being introduced into the container; and
   a sealing member that seals the container by closely contacting an outer periphery of the lamp-protective tube at a portion of the container where the lamp-protective tube is supported,
   characterized in that the ultraviolet treatment apparatus further comprises:
   a light-shielding strip made of a ultraviolet-shielding material and having resiliency, the light-shielding strip comprising: a main light-shielding portion having a length according to at least a circumferential length of an inner periphery of the lamp-protective tube; and first and second overlap portions extending from respective ones of both ends of the main light-shielding portion in a longitudinal direction with each forming a non-parallel convergence shape,
   wherein the light-shielding strip, rolled in the longitudinal direction, is disposed in the lamp-protective tube so as to closely fit to the inner periphery of the lamp-protective tube and positioned so as to oppose to the sealing member.

2. The ultraviolet treatment apparatus as claimed in claim 1, wherein the main light-shielding portion of the light-shielding strip has two sides approximately parallel with each other, and each of the first and second overlap portions forms at least one non-parallel convergence shape whose maximum traverse width is equal to or smaller than a width between the two sides of the main light-shielding portion.

3. The ultraviolet treatment apparatus as claimed in claim 1, wherein each of the first and second overlap portions forms an approximate isosceles triangle whose base is contiguous to the main light-shielding portion.

4. The ultraviolet treatment apparatus as claimed in claim 1, wherein every angle formed in the light-shielding strip is rounded.

5. The ultraviolet treatment apparatus as claimed in claim 1, wherein a thickness of the light-shielding strip is in a range of 0.005 mm to 1 mm.

6. The ultraviolet treatment apparatus as claimed in claim 1, wherein a material of the light-shielding strip includes any one of stainless steel, copper, nickel, iron, aluminum, aluminum alloy, gold, silver, molybdenum, titanium, amorphous, Kovar and silicon.

7. The ultraviolet treatment apparatus as claimed in claim 1, wherein a material of the light-shielding strip includes any one of stainless steel, copper, nickel, iron, aluminum, aluminum alloy, silver, molybdenum, titanium, amorphous, Kovar and silicon, and wherein a surface of the light-shielding strip is plated with gold.

8. The ultraviolet treatment apparatus as claimed in claim 1, wherein the sealing member is an O-ring.

9. The ultraviolet treatment apparatus as claimed in claim 1, wherein the object to be treated is liquid.

10. A light-shielding component to be employed in an ultraviolet treatment apparatus which comprises: an ultraviolet lamp; a lamp-protective tube that inserts the ultraviolet lamp therein; a container that accommodates and supports the lamp-protective tube with at least one end of the lamp-protective tube exposed to an exterior, an object to be treated being introduced into the container; and a sealing member that seals the container by closely contacting an outer periphery of the lamp-protective tube at a portion of the container where the lamp-protective tube is supported, the light-shielding component comprising:
    a light-shielding strip made of a ultraviolet-shielding material and having resiliency, the light-shielding strip comprising: a main light-shielding portion having a length according to at least a circumferential length of an inner periphery of the lamp-protective tube; and first and second overlap portions extending from respective ones of both ends of the main light-shielding portion in a longitudinal direction with each forming a non-parallel convergence shape,
    wherein, when the light-shielding component is employed in the ultraviolet treatment apparatus, the light-shielding strip, rolled in the longitudinal direction, is disposed in the lamp-protective tube so as to closely fit to the inner periphery of the lamp-protective tube and positioned so as to oppose to the sealing member.

11. The light-shielding component as claimed in claim 10, wherein the main light-shielding portion of the light-shielding strip has two sides approximately parallel with each other, and each of the first and second overlap portions forms at least one non-parallel convergence shape whose maximum traverse width is equal to or smaller than a width between the two sides of the main light-shielding portion.

12. The light-shielding component as claimed in claim 10, wherein each of the first and second overlap portions forms an approximate isosceles triangle whose base is contiguous to the main light-shielding portion.

13. The light-shielding component as claimed in claim 10, wherein every angle formed in the light-shielding strip is rounded.

14. The light-shielding component as claimed in claim 10, wherein a thickness of the light-shielding strip is in a range of 0.005 mm to 1 mm.

15. The light-shielding component as claimed in claim 10, wherein a material of the light-shielding strip includes any one of stainless steel, copper, nickel, iron, aluminum, aluminum alloy, gold, silver, molybdenum, titanium, amorphous, Kovar and silicon.

16. The light-shielding component as claimed in claim 10, wherein a material of the light-shielding strip includes any one of stainless steel, copper, nickel, iron, aluminum, aluminum alloy, silver, molybdenum, titanium, amorphous, Kovar and silicon, and wherein a surface of the light-shielding strip is plated with gold.

\* \* \* \* \*